(12) United States Patent
Wu et al.

(10) Patent No.: US 7,824,714 B2
(45) Date of Patent: Nov. 2, 2010

(54) CHINESE HERB EXTRACT FOR TREATING DEMENTIA AND PREPARATION METHOD THEREOF

(75) Inventors: Rey-Yuh Wu, Xizhi (TW); Tzung-Hsien Lai, Xizhi (TW); Yau-Jan Chyan, Xizhi (TW); Chia-Yu Yen, Xizhi (TW)

(73) Assignee: Development Center for Biotechnology (TW)

( * ) Notice: Subject to any disclaimer, the term of this patent is extended or adjusted under 35 U.S.C. 154(b) by 186 days.

(21) Appl. No.: 12/139,304

(22) Filed: Jun. 13, 2008

(65) Prior Publication Data

US 2009/0324751 A1      Dec. 31, 2009

(51) Int. Cl.
*A61K 36/00* (2006.01)
(52) U.S. Cl. ..................................... 424/725
(58) Field of Classification Search ............... None
See application file for complete search history.

(56) References Cited

U.S. PATENT DOCUMENTS

| | | | | |
|---|---|---|---|---|
| 4,797,421 | A * | 1/1989 | Ariga et al. | 420/545 |
| 5,531,991 | A * | 7/1996 | Cheng et al. | 424/725 |
| 6,541,522 | B2 * | 4/2003 | Inman et al. | 514/568 |
| 7,083,811 | B2 | 8/2006 | Jung et al. | |
| 2002/0058708 | A1 * | 5/2002 | Inman et al. | 514/568 |
| 2002/0146467 | A1 | 10/2002 | Jung et al. | |
| 2004/0014682 | A1 * | 1/2004 | Ravagnan et al. | 514/25 |
| 2004/0052879 | A1 * | 3/2004 | Ravagnan et al. | 424/762 |
| 2005/0042314 | A1 * | 2/2005 | Wu | 424/773 |
| 2005/0142224 | A1 * | 6/2005 | Gong et al. | 424/728 |
| 2006/0147557 | A1 * | 7/2006 | Wu et al. | 424/725 |

FOREIGN PATENT DOCUMENTS

| | | | |
|---|---|---|---|
| CN | 1215728 | | 5/1999 |
| CN | 1159015 C | | 5/2002 |
| CN | 1582975 | | 2/2005 |
| CN | 1621078 | | 6/2005 |
| CN | 1742968 | | 3/2006 |
| CN | 101125154 | * | 2/2008 |
| CN | 101255180 | * | 9/2008 |
| JP | 2005-082495 | | 3/2005 |

OTHER PUBLICATIONS

Lv et al. Food Chem. 2007. vol. 104, pp. 1678-1681.*
Wang et al. Neurosci. 2007. vol. 149, pp. 739-746.*
Francis, P.T., et al., The Cholinergic Hypothesis of Alzheimer's Disease: a Review of Progress, J. Neurol. Neurosurg. Psychiatry 66:137-147 (1999).
Selkoe, D.J., Alzheimer's Disease: Genes, Proteins, and Therapy, Physiol. Rev. 81:741-766 (2001).
Hardy, J., et al., The Amyloid Hypothesis of Alzheimer's Disease: Progress and Problems on the Road to Therapeutics, Science 297:353-356 (2002).
Peng, Y., et al., Progress in studies of TCM on Prevention and Treatment of Alzheimer's Disease, World Science and Technology/Modernization of Traditional Chinese Medicine and Materia Medica 7(5):63-67 and 86 (2005).
Wang, J., et al., Study on Optimization of Microwave-assisted Extraction Process for Active Ingredients in Radix Polygoni Multiflori with Uniform Design, Zhongcaoyao (Chinese Traditional and Herbal Drugs) 34(4):314-317 (2003).
Zhang, T., et al., Preparation of National Certified Reference Materials of Active Compounds from Natural Products by CCC, Journal of Liquid Chromatoraphy & Related Technologies, 26(9 & 10):1565-1577 (2003).
Yan, X., Isolation and Identification of Stillbene Glycoside from Polygonum multiflorum Thunb. Shangai Diyi Yixueyuan Xuebao 8(2):1263-6 (1981).
Zhang, L., et al., Effects of Tetrahydroxystilbene Glucoside on Cholinergic System in Dementia Rats Model Induced by Ibotenic Acid. Clin. Pharm. J. 40(10):749-752 (2005).
Kakuda, T., Cerebral Neuroprotective Effects of Green Tea Components, Theanine and Catechins, Foods & Food Ingredients Journal of Japan 191:51-55 (2001).

* cited by examiner

*Primary Examiner*—Christopher R. Tate
(74) *Attorney, Agent, or Firm*—Husch Blackwell LLP; Robert C. Haldiman (57) ABSTRACT

The present invention relates to a *Polygonum multiflorum* extract and the preparation process thereof. The *Polygonum multiflorum* extract of the present invention mainly comprises 2,3,5,4'-tetrahydroxystilbene-2-O-β-D-glucoside and catechin. The present invention also relates to the use of the *Polygonum multiflorum* extract of the present invention for the treatment or prevention of dementia.

24 Claims, 4 Drawing Sheets

CHINESE HERB EXTRACT FOR TREATING DEMENTIA AND PREPARATION METHOD THEREOF

FIELD OF THE INVENTION

The present invention relates to a Chinese herb extract and the preparation method thereof. The present invention also relates to the use of the extract and active fractions for the treatment or prevention of dementia, such as Alzheimer's disease.

BACKGROUND OF THE INVENTION

Dementia is the progressive decline in cognitive function due to damage or a disease in the brain beyond what might be expected from normal aging. The most well-known type of dementia is Alzheimer's disease.

Alzheimer's disease (AD) is an increasingly prevalent form of neurodegeneration that accounts for approximately 50%-60% of the overall cases of dementia among people over 65 years of age. It currently affects an estimated 24 million people worldwide owing to the relative increase of elderly people in the population. Its prevalence is likely to increase over the next 2 to 3 decades. AD is a progressive disorder with a mean duration of around 8.5 years between onset of clinical symptoms and death. Death of pyramidal neurons and loss of neuronal synapses in brain regions associated with higher mental functions results in the typical symptoms, characterized by gross and progressive impairment of cognitive function (see Francis, P. T., et al., *J. Neurol. Neurosurg. Psychiatry* (1999) 66: 137-147). Clinical signs of Alzheimer's disease are characterized by progressive cognitive deterioration, together with declining activities of daily living and by neuropsychiatric symptoms or behavioral changes.

Neuropathologically, the major hallmarks of AD are the presence of two characteristic lesions: the amyloid senile plaque and neurofibrillary tangle (NFT). While the plaque is deposited extraneuronally, the tangle is observed intraneuronally in the post-mortem brain. One of the major components of the amyloid plaque core is the pathologically deposited small amyloid-beta-peptide (Aβ), which is cleaved by secretases from amyloid precursor protein (APP) (see Selkoe, D. J., *Physiol. Rev.* (2001) 81: 741-766; Hardy, J. and Selkoe, D. J., *Science* (2002) 297: 353-356). Aβ, a self-aggregating peptide of 39-43 residues (MW~4 kDa), is synthesized as part of the larger APP (110-120 kDa). APP is a type I integral membrane glycoprotein with a large N-terminal extracellular domain, a single transmembrane domain and a short cytoplasmic tail. The AP region spans portions of the extracellular and transmembrane domains of APP. The most common hypothesis for the participation of APP in neuronal cell death in AD is the amyloid hypothesis. This hypothesis postulates that plaque amyloid depositions or partially aggregated soluble Aβ trigger a neurotoxic cascade, thereby causing neurodegeneration similar to AD pathology (see Selkoe, D. J., *Physiol. Rev.* (2001) 81: 741-766; Hardy, J. and Selkoe, D. J., *Science* (2002) 297: 353-356).

Currently available medications can help reduce the symptoms of the disease, but they cannot change the course of the underlying pathology. There is currently no cure for Alzheimer's disease. There is still a need to provide a method for the treatment and/or prevention of age-related dementia, especially Alzheimer's disease.

*Polygonum multiflorum* is also commonly known as shou wu, he shou wu, fo-ti, fo-ti-teng, Chinese knotweed, climbing knotweed, flowery knotweed, fleece flower, and the like. He Shouwu, a Chinese man who is reputed to have lived until the age of 132, is the first consumer of this herb to be reported. *Polygonum multiflorum* root tuber is traditionally used in Chinese medicines as a tonic and an anti-aging remedy, particularly for hair loss and premature greying of hair. *Polygonum multiflorum* is bitter, sweet, and astringent and has a slight warming effect when ingested. It was used as a principal drug or main component of restorative drugs. The major origins of *Polygonum multiflorum* are He-nan, Gueizhou, Sih-chuan, Hu-nan, Shan-dong, etc. According to Chinese literature, the earliest record of the utilization of *Polygonum multiflorum* can be traced to the Han dynasty (206 B.C.-220 A.D.).

It has been proven that the extracts of *Polygonum multiflorum* have the effects of prolonging the life cycle of diploid cells, prolonging the life of fruit flies and aging pelicans, reducing the level and activity of superoxidase dismutase (SOD), and increasing the DNA repair activity in aging organisms (Peng, Y., et al., *World Science and Technology/Modernization of Traditional Chinese Medicine and Materia Medica* (2005) 7(5):63-67 and 86).

US 2002/146467 A1 and U.S. Pat. No. 7,083,811 B2 disclose herbal compositions for the prevention and treatment of dementia comprising Polygoni multiflori Radix (*Polygonum multiflorum* Thunberg) and other medicinal herbs. CN 1582975 discloses a Chinese medicine for treating cerebrovascular disease and senile dementia which is prepared from five Chinese medicinal materials including fleece flower root, lotus leaf, earthworms, etc., through decocting and extracting in alcohol and then drying. CN 1621078 relates to a Chinese herbal composition, which is prepared from red sage, freeze-dried fresh pilose antler, ginsenoside, fleece flower root, sealwort, haw and rhubarb, for treating hypophrenia and dementia. CN 1742968 relates to a medicine for curing vascular dementia, which is prepared from the Chinese medicinal materials of flowery knotweed root, astragalus root, salvia root, ligusticum root, acorus root, alphinia fruit, ginkgo leaf total flavone, earthworms, leeches and gastrodia root.

Figure 1:
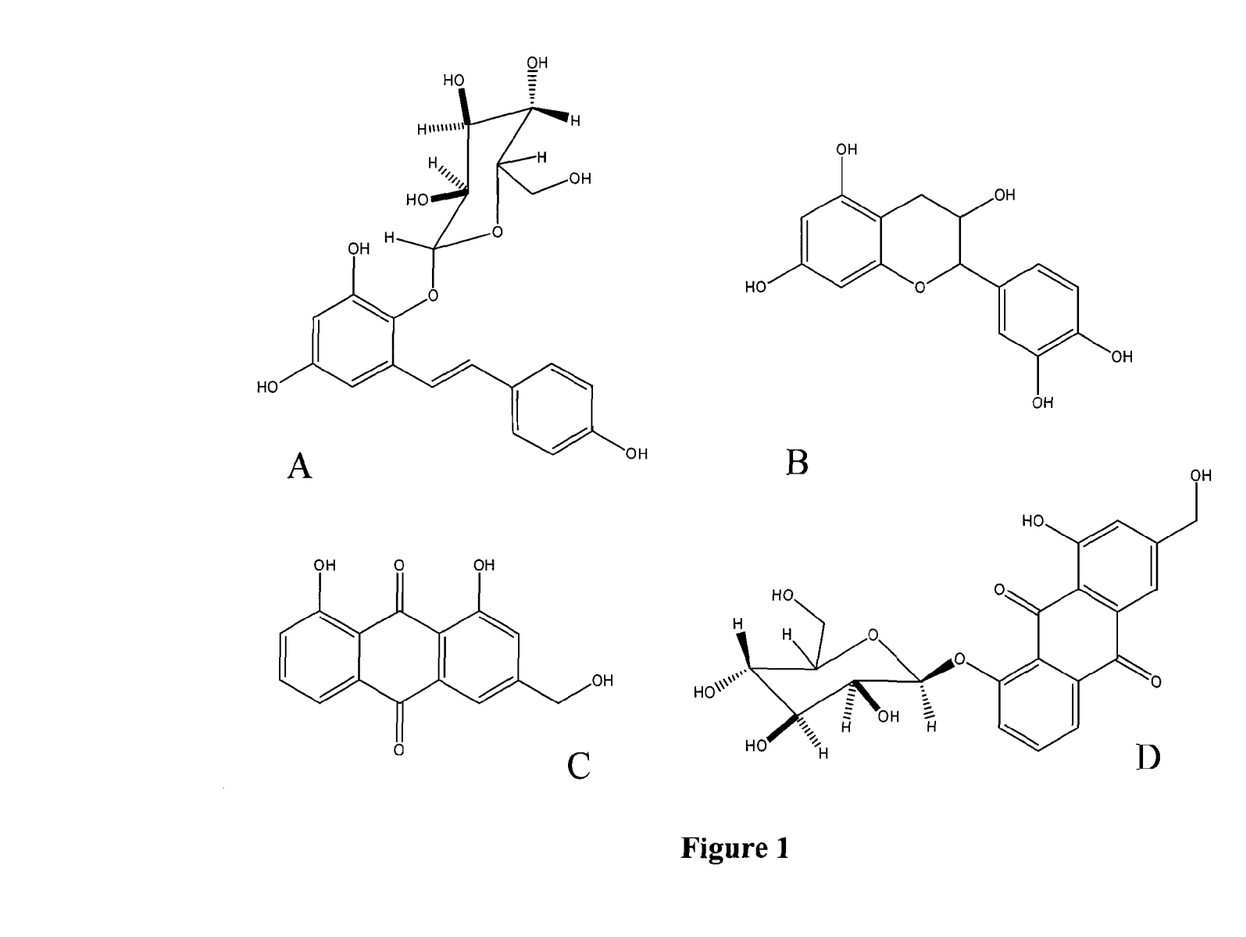
FIG. 1 shows the chemical structures of (A): 2,3,5,4'-tetrahydroxystilbene-2-O-β-D-glucoside (TSG); (B): catechin; (C): emodin (EMD); and (D): emodin-8-O-β-D-glucoside (EMDG).

One of the major components of *Polygonum multiflorum* is 2,3,5,4'-tetrahydroxystilbene-2-O-β-D-glucoside (TSG) as shown in FIG. 1A. TSG can be extracted and isolated using the microwave-assisted extraction process (see Wang, J. et al., (2003) *Zhongcaoyao* 34(4): 314-317), countercurrent technology (see Zhang, T. et al., *Journal of Liquid Chromatography & Related Technologies* (2003) 26(9 & 10): 1565-1577) and the method using liquid-phase extraction and chromatography (see Yan, X., *Shanghai Diyi Yixueyuan Xuebao* (1981) 8(2): 123-6, and CN 1215728). CN 1159015C discloses the utilization of reverse-phase chromatography to isolate the stilbene glucoside compound extracted from *Polygonum multiflorum* by chloroform and then by ethanol. It was proven in animal experiments that the stilbene glucoside compound is capable of preventing the damage of brain cells caused by β-amyloid protein and hydrogen peroxide, and increasing the memory capacity in mice having scopolamine dementia and Aβ dementia. Zhang, L. et al., (*Clin. Pharm. J*, 2005, 40(10): 749-752) discovered that 2,3,5,4'-tetrahydroxystilbene-2-O-β-D-glucoside (TSG) in *Polygonum multiflorum* has the effect of treating cholinergic damage in rats, and that, at a dose as low as 30 mg/kg, TSG can increase choline-acetyltransfertase (ChAT) activity and improve M-cholinergic receptor binding capacity. CN 1159015C also teaches that 3,4',5-trihydroxy-2-stilbenyl beta-D-glucoside can be used as an agent for treating Alzheimer's disease, vascular dementia and impairment of cognitive function.

Green tea is also reported to be capable of preventing the incidence of stroke (see Kakuda, T., *Foods & Food Ingredients Journal of Japan* (2001) 191: 51-55). It is found that catechin in green tea has a radical scavenging effect and can indirectly prevent dementia. JP 2005-082495 discloses that catechin and aminobutyric acid (GABA) contained in green tea have efficacy in the improvement of memory and the treatment of dementia and mental disorders.

Generally, the complexity of herbal medicines exists in not only the diversity of ingredients, but also the putative interactions between herbs. Therefore, the actions of traditional herbal medicine are totally different from those of modern western medicine, with its single-target and single-drug relationship. In view of the difficulty in identifying all the components in a simple Chinese herb, it is difficult to determine whether a synergistic and/or complementary effect is achieved by the active ingredients contained therein by scientific methods. In order to study the efficacy of a Chinese herb and to produce a therapeutic agent from a Chinese herb, it is necessary to develop an effective method to isolate, identify and purify the active ingredients in the herb.

Traditionally, the crude material of *Polygonum multiflorum* must be processed before use so as to remove the components emodin and physcion, which may cause the side effect of diarrhea, from the material. In the traditional processing method, dried *Polygonum multiflorum* is soaked and heated by steam in black soybean juice, and then is dried to obtain a product called "Radix Polygoni Multiflori." However, during the processing, the therapeutically active ingredient will be degraded. Thus, there is still a need to develop an efficient method to process *Polygonum multiflorum*. Furthermore, in order to improve the efficacy of *Polygonum multiflorum* extract, it is necessary to develop an economical and efficient method to obtain a product that comprises maximum amounts of TSG and catechin, and a minimum amount of emodin.

SUMMARY OF THE INVENTION

One of the purposes of the present invention is to provide a process for preparing *Polygonum multiflorum* extracts.

Another purpose of the present invention is to provide a *Polygonum multiflorum* extract.

Another purpose of the present invention is to provide a composition comprising the *Polygonum multiflorum* extract of the present invention.

Still another purpose of the present invention is to provide a method for the prevention or treatment of dementia, such as aging-related dementia, Alzheimer's disease, vascular dementia or minor mental and intellectual disorders, in a subject, comprising administrating the composition of the present invention to a subject in need thereof.

A further purpose of the present invention is to provide a use of the *Polygonum multiflorum* extract of the present invention in the manufacture of a medicament for the prevention or treatment of dementia, such as aging-related dementia, Alzheimer's disease, vascular dementia or minor mental and intellectual disorders.

The present invention is described in detail in the following sections. Other characterizations, purposes and advantages of the present invention can be easily found in the detailed descriptions and claims of the invention.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The term "dementia" as used herein denotes the progressive decline in cognitive function due to damage or disease in the brain beyond what might be expected from normal aging, such as aging-related dementia, Alzheimer's disease, vascular dementia, minor mental and intellectual disorders, and the like.

The term "preventing" or "prevention" as used herein refers to delaying the onset of the symptoms of a susceptible subject or reducing the occurrence of a disease.

The term "treating" or "treatment" as used herein denotes reducing and/or improving the symptoms of a susceptible subject.

The term "subject" as used herein denotes animals, especially mammals. In one preferred embodiment, the term "subject" denotes "humans."

The term "therapeutically effective amount" as used herein refers to the amount of an active ingredient used alone or in combination with other treatments/medicaments for treating dementia that shows therapeutic efficacy.

The term "carrier" or "pharmaceutically acceptable carrier" refers to diluents, excipients, acceptors or analogues, which are well known to persons of ordinary skill in the art, for manufacturing pharmaceutical compositions.

The term "*Polygonum multiflorum* herb" refers to the dried roots, leaves, stems, and/or the whole body of the plant *Polygonum multiflorum*, preferably, the roots of the plant.

The term "alcohol solution" refers to an absolute alcohol or a solution prepared by mixing alcohol with water. According to the invention, the alcohol has an straight or branched alkyl portion having one to six carbon atoms, preferably having one to four carbon atoms, and more preferably having one to three carbon atoms. For example, the alcohol is methanol, ethanol, isopropanol or a mixture thereof. Preferably, the alcohol is methanol or ethanol.

Unless otherwise required by the context, singular terms shall include the plural and plural terms shall include the singular.

The Preparation Processes

The process of the present invention for preparing a *Polygonum multiflorum* extract comprises the steps of:

a) extracting the *Polygonum multiflorum* herb with an alcohol solution to obtain a crude extract;

b) diluting the crude extract obtained by step a) with water to obtain a diluted crude extract;

c) loading the diluted crude extract of step b) into a resin column;

d) eluting the *Polygonum multiflorum* extract from the column; and e) colleting the eluted fraction to obtain the refined *Polygonum multiflorum* extract.

According to the process of the present invention, the concentration of alcohol in the alcohol solution used in step a) is about 10 to 100 v/v %. In one preferred embodiment, the alcohol solution is a methanol solution of about 10 to 100 v/v %, preferably about 20 to 95 v/v %, most preferably about 20 to 50 v/v %. In another preferred embodiment, the alcohol solution is an ethanol solution of about 10 to 95 v/v %, preferably about 10 to 30 v/v %, most preferably about 20 v/v %.

According to the process of the present invention, the crude extract of step a) can be obtained by any conventional extraction methods, such as decoction, dipping, sonication, stirring, agitation or the mixture thereof. The extraction period is about 1 to about 24 hours, preferably about 12 to 24 hours, and most preferably more than about 17 hours. The extraction temperature is about 5 to 95° C., preferably about 10 to 30° C., most preferably at room temperature. The extraction pH is about 2.5 to 9.1, preferably about 2.5 to 5.3, most preferably about 5.3. In one preferred embodiment, the *Polygonum multiflorum* herb is extracted by a cool-extraction method (sonication for 1 hour and stirring for 16 hours at room temperature).

According to the process of the present invention, in step b), the crude extract is diluted with water so that the concentration of alcohol in the diluted extract becomes about 1 to 10 v/v %, preferably about 2 to 5 v/v %. In one preferred embodiment, the alcohol concentration of the diluted crude extract is about 2 v/v %. In another preferred embodiment, the alcohol concentration of the diluted crude extract is about 5 v/v %.

According to the process of the present invention, the resin used in step c) is selected from, but is not limited to, macroporous resins and gel resins. The macroporous resin is preferably selected from the DIAION series, Amberlite series and Dowex adsorbents, more preferably the DIAION series. The gel resin is preferably selected from the Sephadex series, Toyopearl and Sephacryl, more preferably the Sephadex series. In one preferred embodiment, the resin is DIAION HP-20. In another preferred embodiment, the resin is Sephadex LH-20.

According to the process of the present invention, prior to the application of the diluted crude extract into the column of step c), the resin is washed with a washing solution which has an alcohol concentration identical to that of the diluted crude extract obtained from step b).

According to the process of the present invention, prior to the elution step d), the column is washed with a washing solution which has an alcohol concentration identical to that of the diluted crude extract obtained from step b).

According to the process of the present invention, in step d), in order to obtain the *Polygonum multiflorum* extract, the column is eluted with an alcohol solution of about 10 to 100 v/v %, preferably about 30 to 70%, and more preferably about 35 to 50%, and then eluted with an acetone solution of about 70 to 100 v/v %. The alcohol solution may be a series of alcohol solutions having incremental concentrations of alcohol. In one preferred embodiment, the column is eluted with a 50 v/v % methanol solution, then 100% methanol, and finally 100% acetone. In another preferred embodiment, the column is eluted with a 50 v/v % ethanol solution, then a 95 v/v % ethanol solution, and finally 100% acetone. In still another preferred embodiment, the column is eluted with a 35 v/v % ethanol solution, then a 50 v/v % ethanol solution, then a 75 v/v % ethanol solution, then a 95 v/v % ethanol solution, and finally 70 v/v % acetone.

The present invention provides an advantageous process for preparing *Polygonum multiflorum* extracts. The *Polygonum multiflorum* extracts obtained by the process of the present invention contain more 2,3,5,4'-tetrahydroxystilbene-2-O-β-D-glucoside (TSG) and catechin, and less emodin (EMD) and emodin-8-O-β-D-glucoside (EMDG) than the traditionally processed *Polygonum multiflorum* extracts. The *Polygonum multiflorum* extract prepared by the process of the present invention preferably contains mainly TSG and catechin. The *Polygonum multiflorum* extract prepared by the process of the present invention more preferably contains more than about 65 w/w % of TSG, more than about 5 w/w % of catechin, less than about 0.5 w/w % of EMD and less than about 0.2 w/w % of EMDG. The *Polygonum multiflorum* extract prepared by the process of the present invention most preferably contains about 65 to 85 w/w % of TSG and about 5 to 10 w/w % of catechin.

According to the process of the present invention, the recovery rate of tetrahydroxy stilbene in the *Polygonum multiflorum* extract compared to that in the *Polygonum multiflorum* crude extract is greater than about 80%, preferably greater than about 90%, more preferably greater than about 95%, and most preferably greater than about 97%. The recovery rate of catechin in the *Polygonum multiflorum* extract compared to that in the *Polygonum multiflorum* crude extract is greater than about 70%, preferably greater than about 75%, and more preferably greater than about 80%.

According to the process of the present invention, the eluted extract obtained in step e) may be concentrated by any conventional concentration methods for solutions, such as using a pressure-reducing rotary evaporator.

Compositions

The present invention provides a composition comprising a therapeutically effective amount of the *Polygonum multiflorum* extracts of the present invention.

The composition of the present invention can be administrated to a subject by any suitable administration route, such as oral administration. Suitable formulations include but are not limited to tablets, lozenges, hard or soft capsules, aqueous or oily suspensions, emulsions, dispersible powders or granules, syrups or elixirs. If necessary, it may be sterilized or mixed with any pharmaceutically acceptable carriers, such as stabilizers, wetting agents and the like.

The compositions of the invention may be obtained by conventional procedures using conventional pharmaceutical excipients that are well known in the art. Thus, compositions intended for oral use may contain, for example, one or more coloring, sweetening, flavoring and/or preservative agents.

The composition of the present invention may be used in combination with other current anti-dementia agents, such as cholinesterase inhibitors (for example, Reminyl, Exelon, Aricept and Cognex and memantine) in AD treatment.

Utilities

The compositions of the present invention can be used for the prevention or treatment of dementia, such as aging related dementia, Alzheimer's disease, vascular dementia, minor mental and intellectual disorders, and the like.

Persons skilled in the art should have no difficulty choosing the suitable routes and the dosages for treatments. According to the present invention, the preferred route is oral administration. Dosage will depend on the nature and condition of the disorder, age and health condition of the patient, administration route and any previous treatment. Persons skilled in the art should know that dosage may vary depending on the individual's age, size, health condition and other related factors.

In one preferred embodiment, the optimum dosages of the *Polygonum multiflorum* extracts of the present invention are about 1 to about 25 mg/kg body weight.

The following examples are provided to aid those skilled in the art in practicing the present invention. Even so, the examples should not be construed as unduly limiting the present invention, as modifications to and variations on the embodiments discussed herein may be made by those having ordinary skill in the art without departing from the spirit or scope of the present discovery.

EXAMPLES

Preparation of *Polygonum multiflorum* Extracts

Dried *Polygonum multiflorum* plants were ground and then mixed and dipped in a high-polarity solvent, e.g., water, methanol, ethanol, isopropanol or a mixture thereof, for 24 hours. The mixture was filtered with a mesh or filter to remove the plant residues and a clear yellowish-brown solution (*Polygonum multiflorum* crude extract) was obtained.

Macroporous resins or gel resins were packed into an isolation column. The column may be made of glass, stainless steel or a high-molecular polymer, such as PP. If macroporous resins were used, the resins were packed into the column by dry packing. If gel resins were used, the resins were dipped in water and then packed into the column after swelling. The weight of resins is more than ten-fold the weight of the original dried plants. The packed column was washed with 100% methanol or 95 v/v % ethanol solution to remove the impurity and equilibrated with 2 to 5 v/v % alcohol-water solution.

A suitable amount of *Polygonum multiflorum* crude extract was diluted with water until the concentration of the solvent was about 2 to 5 v/v %. The diluted solution was pumped into the isolation column. After all the diluted solution was loaded into the column, the column was washed with 2 to 5 v/v % alcohol solution having a volume five-fold the volume of the column, and then eluted with solvent-water mixtures in different ratios. The eluted fractions were concentrated with a pressure-reducing rotary evaporator and freeze-dried to obtain extract powders.

Method for Composite Analysis of the *Polygonum multiflorum* Extracts

Instruments and equipment: HPLC System (Shimadzu HPLC system, including SCL-10Avp system controller, LC-10ATvp pump, FCV-10ALvp four-way valve, SIL-10ADvp autosampler, SPD-M10Avp diode array detector, Alltech 2000 ELSD Evaporetive light-scattering detector and ERC-3415αdegasser)

Analysis column: Cosmosil C18-5MS (4.6×250 mm)
Conditions:
Flow rate: 1.0 ml/min
Analysis time: 60 min
Sample amount: 10 µl
PDA conditions: Sampling period: 0.64 sec; Wavelength range: 190-370 nm;
Channels: 254 nm
ELSD conditions: Temperature 100° C.; Nitrogen flow rate: 3.0 ml/min
Control samples: TSG, catechin, EMDG and emodin
Mobile phase: B=100% acetonitrile; C=methanol; D=10 mM $NH_4OAc$, pH 3.05

| Time (min) | B (ACN) | C (MeOH) | D (10 mM $NH_4OAc$, pH 3.05) |
|---|---|---|---|
| 0 | 0 | 10 | 90 |
| 5 | 0 | 10 | 90 |
| 35 | 100 | 0 | 0 |
| 50 | 100 | 0 | 0 |
| 53 | 0 | 10 | 90 |
| 60 | 0 | 10 | 90 |

Method for Testing the Activities of the *Polygonum multiflorum* Extracts

The activities of the *Polygonum multiflorum* extracts were tested by utilizing an animal model according to Nabeshima, T. and Nitta, A. (Tohoku J. Exp. Med., 1994, 174(3):241-249).

Alzheimer's disease rats induced by cerebral ventricular injection of amyloid peptide (Aβ40) were used to evaluate the therapeutic effect of the *Polygonum multiflorum* extract on the intellectual and learning disability induced by Amyloid β-peptide 1-40 (Aβ 1-40). Moreover, in vitro activity screen technology utilizing neuron antagonistic amyloid Aβ neurotoxin was used to analyze the bioactivity of the purified substance in the *Polygonum multiflorum* extract.

Example 1

The Influence of Extraction Temperatures and Solvents 5 g of *Polygonum multiflorum* (PM) powders were added into about 50 ml water and extracted in 100° C. water bath for one hour. The mixture was centrifuged at room temperature at the speed of 8,000 rpm for 15 minutes, and then filtrated by vacuum filtration using No. 1 filter paper. 34 ml filtrate (PMWH) was collected.

2.5 g of *Polygonum multiflorum* powders were cool-extracted (sonication for 1 hour and rotated at a speed of 45 rpm for 16 hours at room temperature) with four different solvents, i.e., double distilled water, 20 v/v % ethanol solution, 50 v/v % ethanol solution and 95 v/v % ethanol solution. Then, the mixtures were centrifuged at room temperature at the speed of 3,000 rpm for 15 minutes, and then filtrated by vacuum filtration using No. 1 filter paper to collect the first extracts (PMWL-1, PM20EL-1, PM50EL-1 and PM95EL-1). The remaining residues were extracted again by the cool-extraction steps described above and the second extracts (PMWL-2, PM20EL-2, PM50EL-2 and PM95EL-2) were collected. The production rates for each of the extracts were analyzed and the amounts of emodin (EMD), emodin-8-O-β-D-glucoside (EMDG) and 2,3,5,4'-tetrahydroxystilbene-2-O-β-D-glucoside (TSG) in the extracts were analyzed by HPLC. The production rates for each extraction method and batch were summarized in Table 1.

TABLE 1

Extraction rates utilizing different extraction methods and multiple extractions

| | Sample | | | |
|---|---|---|---|---|
| | The first extracts | | The second extracts | |
| Extraction method | Amount of extract (mg/ml) | Extraction rate (%) | Amount of extract (mg/ml) | Extraction rate (%) |
| PMWH (hot water extraction) | 34 | 23.1 | — | — |
| PMWL (room-temperature water extraction) | 24.9 | 19.1 | 3.7 | 3.4 |
| PM20EL (room-temperature 20% ethanol extraction) | 30.3 | 23.1 | 5.5 | 5.1 |
| PM50EL (room-temperature 50% ethanol extraction) | 33.4 | 26.2 | 5.1 | 4.5 |
| PMEL (room-temperature 95% ethanol extraction) | 20.7 | 19.7 | 2.5 | 2.8 |

As shown in Table 1, the extraction rate of hot water extraction is about 20% higher than that of room-temperature water extraction. If ethanol solutions are used as extractants, the method utilizing 50% ethanol solution has the highest extraction rate. In summary, the extraction rates in the first extractions are about 19 to 26%, and the extraction rates in the second extractions are only 3 to 5%. The analytic results of the amount of EMD, EMDG and TSG were summarized in Table 2.

TABLE 2

The amounts of EMD, EMDG and TSG in different extracts

| Amount of the ingredient (mg) | PMWH | PMWL | PM20EL | PM50EL | PM95EL |
|---|---|---|---|---|---|
| EMD | 0.00 | 0.13 | 0.00 | 1.88 | 3.88 |
| EMDG | 1.34 | 0.00 | 0.00 | 0.00 | 8.72 |
| TSG | 20.40 | 28.78 | 32.61 | 56.28 | 40.08 |

The amounts of TSG in the extract extracted by room-temperature water are about 40% higher than that extracted by hot water. The extract extracted by room-temperature water contains EMD, whereas the extract extracted by hot water contains EMDG. When extracting by ethanol solution, the extract extracted by 50% ethanol solution contains the highest amount of TSG. However, the amounts of EMD and EMDG increased with the increase of the concentration of ethanol. Although, the extract extracted by 20% ethanol solution does not have the highest amount of TSG, it does not contain EMD or EMDG. Therefore, by evaluating the TSG extraction rate and the quality of the extract, the extraction method utilizing 20% ethanol solution at room temperature has the greatest benefit.

Example 2

The Influence of the Ratio of Extractants and pH

Three different solvents (10 v/v %, 20 v/v % and 30 v/v % ethanol solution) were prepared. 2 g of *Polygonum multiflorum* powders were added into 20 ml of each solvent, and three tubes of mixtures were prepared for each solvent. The three tubes of each solvent were adjusted with NaOH and HCl to pH 2.5, 5.3 and 9.1, respectively. Then, the tubes were sonicated for one hour and rotated at a speed of 45 rpm for 16 hours. Each sample was centrifuged at the speed of 3,000 rpm for 15 minutes, and the supernatants were collected. The ingredient analysis of the supernatants was summarized in Table 3.

TABLE 3

The amounts of EMD, EMDG and TSG in the *Polygonum multiflorum* (PM) extracts extracted utilizing different solvents and pH

| | pH | | | | | | | | |
|---|---|---|---|---|---|---|---|---|---|
| | 2.5 | | | 5.3 | | | 9.1 | | |
| | Solvent (ethanol concentration) | | | | | | | | |
| | 10% | 20% | 30% | 10% | 20% | 30% | 10% | 20% | 30% |
| | Amount of the ingredient (mg/g PM powder) | | | | | | | | |
| EMD | 0.14 | 0.18 | 0.36 | 0.19 | 0.26 | 0.38 | 1.22 | 1.61 | 2.03 |
| EMDG | 0.98 | 1.05 | 1.20 | 0.00 | 0.00 | 0.00 | 0.60 | 1.04 | 1.60 |
| TSG | 22.12 | 22.01 | 25.20 | 25.75 | 25.35 | 27.24 | 0.00 | 0.00 | 2.43 |

As shown in Table 3, the amount of EMD increased along with the increase of ethanol concentration (10%<20%<30%) at the three pHs. The amount of EMD extracted by 30% ethanol solution is about two-fold that extracted by 20% ethanol solution. TSG is rarely extracted from *Polygonum multiflorum* at pH 9.1 utilizing the three solvents. At pH 5.3 and 2.5, the amounts of extracted TSG were similar, and slightly increased when the concentration of ethanol increased (10%<20%<30%). At pH 5.3, EMDG was not extracted by the three solvents; whereas at pH 2.5 and 9.1, some EMDG was extracted and the amount increased along with the increase of ethanol concentration (10%<20%<30%).

The results of Example 2 suggest that the optimum conditions for the extraction of *Polygonum multiflorum* are utilizing 10 to 20% ethanol solution at pH 5.3. Under this condition, the TSG can be extracted efficiently and a minimum amount of EMD and EMDG will be extracted. When the extraction pH decreased to 2.5, the amount of TSG was decreased about 10%, the amount of EMD was decreased about 30% and the amount of EMDG was increased.

Example 3

Extracting of the Active Ingredients of *Polygonum multiflorum* Utilizing Macroporous Resins 100 g of *Polygonum multiflorum* powders were cool-extracted (sonication for 1 hour and stirring for 16 hours at room temperature) with 1 liter of methanol. The extracted solution was filtrated by vacuum filtration using No. 1 filter paper and 900 ml of filtrate (PM901) was collected.

100 g of DIAION HP-20 resin (Mitsubishi Chemicals) was packed into a chromatographic column (ID=40 mm; L=200 mm), and the column was recycled with 1 liter of methanol for one hour. The column was then washed with 2 liters of 5 v/v % methanol solution. 400 ml of PM901 was diluted with pure water to the final volume of 8 liters, so that the final concentration of methanol became 5%. The diluted solution was loaded into the DIAION column at a flow rate of 15 ml/min, and the unbound fluid was collected. The column was washed with 1 liter of 5 v/v % methanol solution and the washing fluid was combined with the unbound fluid, and then the combined fluid was concentrated to 50 ml by a pressure-reducing rotary evaporator (PM902).

The column was then eluted with 1.5 liters of 50 v/v % methanol solution. The eluted fluid was collected and concentrated to 200 ml by a pressure-reducing rotary evaporator (PM903). The column was further eluted with 1.5 liters of 100% methanol. The eluted fluid was collected and concentrated to 200 ml by a pressure-reducing rotary evaporator (PM904). Finally, the column was eluted with 1 liter of 100% acetone. The eluted fluid was collected and concentrated to 50 ml by a pressure-reducing rotary evaporator (PM905). The amounts and recovery rates of TSG and catechin in the samples (collected before or after column separation) were shown in Table 4.

TABLE 4

The amounts of TSG and catechin in PM901 to PM905 and the recovery rates

| Samples | Total amount of catechin (mg) | Recovery rate of Catechin (%) | Percentage of catechin in the sample (%) | Total amount of TSG (g) | Recovery rate of TSG (%) | Percentage of TSG in the sample (%) |
|---|---|---|---|---|---|---|
| PM901 | 10.8 | 100 | 0.13 | 1.7 | 100 | 21.2 |
| PM902 | 1.6 | 14.8 | 0 | 0 | 0 | 0 |
| PM903 | 8.6 | 79.6 | 0.31 | 1.5 | 88.2 | 54.3 |
| PM904 | 0 | 0 | 0 | 0.1 | 5.8 | 14.6 |
| PM905 | 0 | 0 | 0 | 0 | 0 | 0 |

As shown in Table 4, the percentage of TSG and catechin in the methanol-extracted sample (PM901) is 21.2% and 0.13%, respectively. The extracted sample PM901 can be further refined by column separation with 50% methanol solution to obtain 2.8 g of PM903. The percentage of TSG in PM903 is 54.3%, which is 2.6-fold the original percentage, and the percentage of catechin in PM903 is 0.31%, which is 3-fold the original percentage. The recovery rates of TSG and catechin are 88.2% and 79.6%, respectively.

Example 4

Extracting of the Active Ingredients of *Polygonum multiflorum* Utilizing Macroporous Resins 180.10 g of *Polygonum multiflorum* powders were cool-extracted (sonication for 1 hour and stirring for 16 hours at room temperature) with 1.8 liters of 20 v/v % ethanol solution. The extracted solution was centrifuged at 25° C. at the speed of 8,000 rpm for 15 minutes and then filtrated by vacuum filtration using No. 1 filter paper. 1,840 ml of filtrate (PM20EL) was collected and the amount of solid substance was measured.

300.08 g of DIAION HP-20 resin was packed into a chromatographic column (ID=80 mm; L=295 mm), and the column was recycled with 2.0 liters of 95 v/v % ethanol solution for 1.5 hours. The column was then washed with 4.38 liters of 2 v/v % ethanol solution. 1,533 ml of PM20EL was diluted with pure water to 15,330 ml, so that the final concentration of ethanol became 2%. The diluted solution was loaded into the DIAION column at a flow rate of 15 ml/min, and the unbound fluid was collected. The column was washed with 3.84 liters of 2 v/v % methanol solution and the washing fluid was combined with the unbound fluid, and the total volume of the combined fluid was 16,840 ml (PM801).

The column was then eluted with 6.5 liters of 50 v/v % ethanol solution. The first 200 ml of yellowish-orange colored eluted fluid was collected and the collected fluid was combined with the remaining extraction fluid to be PM802. The amounts and recovery rates of TSG and catechin in the samples (collected before or after column separation) were shown in Table 5.

TABLE 5

The amounts of TSG and catechin in PM20EL, PM801 and PM802 and the recovery rates

| Samples | Total amount of catechin (mg) | Recovery rate of Catechin (%) | Percentage of catechin in the sample (%) | Total amount of TSG (g) | Recovery rate of TSG (%) | Percentage of TSG in the sample (%) |
|---|---|---|---|---|---|---|
| PM20EL | 41.4 | 100.0 | 0.11 | 5.2 | 100.0 | 14.3 |
| PM801 | 0.6 | 1.5 | 0.02 | 0.0 | 0.0 | 0.0 |
| PM802 | 28.9 | 69.9 | 0.32 | 4.8 | 91.2 | 52.3 |

As shown in Table 5, the percentage of TSG and catechin in the 50% ethanol solution-extracted sample (PM20EL) is 14.3% and 0.11%, respectively. The extracted sample PM20EL can be further refined by column separation with 50% methanol elution solution to obtain 9.1 g of PM802. The percentage of TSG in PM802 is 52.3%, which is 3.6-fold the original percentage, and the percentage of catechin in PM802 is 0.32%, which is 3-fold the original percentage. The recovery rates of TSG and catechin are 91.2% and 69.9%, respectively. According to the results of Example 4, the preparation process of the present invention can efficiently separate TSG and catechin, and the loss rates were controlled so that they were as low as 8.8% (TSG) and 30.1% (catechin).

Example 5

Extracting of the Active Ingredients of *Polygonum multiflorum* Utilizing Gel Resins 30 g of Sephadex LH-20 resin (Pharmacia) were packed into a chromatographic column and were recycled with 500 ml of 95 v/v % ethanol solution at a flow rate of 20 ml/min for 2 hours. The column was then washed with 500 ml of 2 v/v % ethanol solution. 132 ml of PM20EL-1 obtained from Example 4 were diluted with M.Q. water to the final volume of 1000 ml. The diluted solution was loaded into the LH-20 column and the unbound light-brownish turbid fluid was collected. The column was washed again with 500 ml of 2 v/v % ethanol solution. The first 150 ml of washing fluid was combined with the unbound fluid and the combined fluid was concentrated to 25 ml (PM211) by a pressure-reducing rotary evaporator. The remaining 345 ml of light yellowish clear washing fluid were collected and concentrated to 10 ml (PM212) by a pressure-reducing rotary evaporator. PM211 and PM212 were combined to be PMLH201.

The column was first eluted with 250 ml of 35 v/v % ethanol solution and 244 ml of eluted fluid (the first 80 ml has a light yellowish color and the remaining 164 ml has a light yellowish-brown color) were collected and concentrated to 25 ml (PMLH202c) by a pressure-reducing rotary evaporator.

The column was then eluted with 250 ml of 50 v/v % ethanol solution and 244 ml of eluted fluid (the first 60 ml has a light yellowish-brown color and the remaining 184 ml has a yellowish-brown color) were collected and concentrated to 25 ml (PMLH203c) by a pressure-reducing rotary evaporator.

The column was then eluted with 250 ml of 75 v/v % ethanol solution and 242 ml of eluted fluid (the first 70 ml has a light yellowish-brown color, the next 56 ml has a yellowish-brown color and the remaining 116 ml has a light orange color) were collected and concentrated to 25 ml (PMLH204c) by a pressure-reducing rotary evaporator.

The column was then eluted with 250 ml of 95 v/v % ethanol solution and 246 ml of eluted fluid (the first 70 ml has a light orange color and the remaining 176 ml is colorless) were collected and concentrated to 25 ml (PMLH205c) by a pressure-reducing rotary evaporator.

Finally, the column was eluted with 250 ml of 70 v/v % acetone solution and 246 ml of eluted fluid were collected and concentrated to 25 ml (PMLH206c) by a pressure-reducing rotary evaporator. The amounts of the solid substance in each concentrated sample (fraction) and the ratio of the active ingredient were analyzed, and the results were shown in Table 6.

As shown in Table 6, the majority of TSG can be eluted by 35 to 50% ethanol solutions, and the total recovery rate was over 97%. Catechin and EMDG can be eluted in the same fractions, but the majority of EMD was eluted by 50% ethanol solution. The results of Example 5 suggest that when LH-20 resin was used as the separation material, the optimum elution solutions are 35 to 40 v/v % ethanol solutions.

Example 6

Cognitive Behavior Evaluation of PM903 by Using Aβ Injection-Induced Alzheimer Rat Model Induction of Neurodegeneration in the Rats Aβ 1-40 infusion rat model is an animal model for fast screening of drugs for treating Alzheimer's disease. The neurodegeneration of the rat model is induced by slowly pumping Aβ 1-40 into the third lateral cerebral ventricule in rats, so that the hippocampus is damaged through the cerebrospinal fluid (CSF) system and the cognitive behavior impairments are developed.

To prepare the Alzheimer's rats, Aβ 1-40 solution was put into Alzet osmotic pumps (Alzet 1002; DURECT Co., USA) and the PE tubes of the brain infusion kits were connected to the pumps. Rats were anesthetized with sodium pentobarbital (45 mg/kg) and were placed in a stereotaxic instrument (STOELTING, USA; Model 51650 ) in order to locate the lateral cerebral ventricule. The brain infusion kits were inserted into the third lateral cerebral ventricule of the rats and the Alzet osmotic pumps were implanted in the subcutaneous area of the back of the rat's neck. The surgical areas were sutured and the rats were placed in cages. In the control group (Sham), the Aβ 1-40 solution in the Alzet osmotic pump was replaced by 35% acetonitrile/0.1% trifluoacetic acid. 8 to 9 days after the implantation, the rats were given a passive avoidance test. 10 to 15 days after the implantation, the cognitive behavior of the rats was evaluated using a Morris water maze. From the day following the implantation, the rats of the

TABLE 6

The amounts of TSG, EMD, EMDG and catechin in each fraction and the recovery rates

| Fraction | Solvent | Amount of solid substance (mg/ml) | Amount of TSG (mg/ml) | Recovery rate of TSG (%) | Ratio of TSG and the solid substance (%) | Amount of EMD (μg/ml) | Ratio of EMD and the solid substance (%) | Amount of EMDG (μg/ml) | Ratio of EMDG and the solid substance (%) | Amount of catechin (mg/ml) | Ratio of catechin and the solid substance (%) |
|---|---|---|---|---|---|---|---|---|---|---|---|
| PM20EL-1 | 20% EtOH | 26.4 | 2.8 | 100 | 10.6 | 8.0 | 0.03 | 0 | 0.00 | 0 | 0.00 |
| PMLH201 | 20% EtOH (unbound) | 84.0 | 0.6 | 4.7 | 0.7 | <3.5 | <0.004 | <5 | <0.01 | 0.7 | 0.83 |
| PMLH202c | 35% EtOH | 8.5 | 6.9 | 53.6 | 81.2 | <3.5 | <0.041 | 7 | 0.08 | 0.7 | 8.24 |
| PMLH203c | 50% EtOH | 7.1 | 5.6 | 43.5 | 78.9 | 21.9 | 0.31 | <5 | <0.07 | <0.5 | <7.04 |
| PMLH204c | 75% EtOH | 3.2 | 0 | 0 | 0 | 4.0 | 0.13 | 0 | 0.00 | 0 | 0.00 |
| PMLH205c | 95% EtOH | 1.2 | 0 | 0 | 0 | 0 | 0.00 | 0 | 0.00 | 0 | 0.00 |
| PMLH206c | 70% Acetone | 10.8 | 0 | 0 | 0 | 0 | 0.00 | 0 | 0.00 | 0 | 0.00 | experiment groups were administrated with placebos, different dosages of PM903 (1 to 25 mg/kg), and 100 mg/kg of PMWH, respectively.

Construction of Passive Avoidance Task

The passive avoidance test was performed according to the step-through method (see Jarvik M. E. and Kopp R. *Psychol Rep.* (1967) Aug; 21 (1):221-224). The apparatus consisted of a light compartment connected to a dark box by a dividing wall containing a guillotine door. In the training session, an acquisition trial was performed as follows: rats were acclimated in the light compartment for 2 min, then the guillotine door was opened. Three seconds later, when the rats crossed over into the dark box, an inescapable electrical shock (0.8 mA, 3 seconds) was delivered. This trial was repeated until acquisition was established. Acquisition was regarded as being established when rats eventually remained in the light compartment for more than 300 seconds to avoid entering the dark box. The rats were removed and returned to the homecage. The data were analyzed by ANOVA.

Construction of Morris Water Maze

In neuroscience, the Morris water maze is a behavioral procedure designed to test spatial memory. It was developed by neuroscientist Richard G. Morris in 1984 (see Morris R. *J Neurosci Methods* (1984) 11 (1): 47-60), and is commonly used today to explore the role of the hippocampus in the formation of said spatial memory.

A cylindrical water pool (160 cm in diameter and 60 cm deep) was filled with water to 35 cm and the temperature of the water was maintained at 23±1° C. The water pool was divided into four quadrants (northwest, southwest, northeast and southeast). A round stainless escape platform was fixed in the "southwest" quadrant hidden 1 cm below the water surface. Visual cues, such as colored shapes, were placed around the pool in plain sight of the animal. A CCD camera connected to a personal computer was placed above the water pool to capture and record the images of the tested rat's path.

Testing of Animal Behavior

Four to five rats were used in each group. The rats were trained for three days, one training session per day, and four rounds per session. Each rat was given 122 seconds to find the escape platform in the "southwest" quadrant in each round. If the rat could not find the escape platform, the rat was guided to the platform. The rat was left to rest for 15 seconds before the next round. The whole testing process including the swimming path and the time taken to reach the platform (latency) was recorded by the computer tracking system. On day four, the escape platform was removed and the time taken for the rats to reach the "southwest" quadrant and to reach other quadrants within 1.5 minutes was calculated. The data of latencies and swimming distances obtained from the first four behavior tests represent the learning and memory ability of the rats. The data were analyzed by ANOVA. The behavior test on day four represents the reference spatial memories of the rats.

Figure 2:
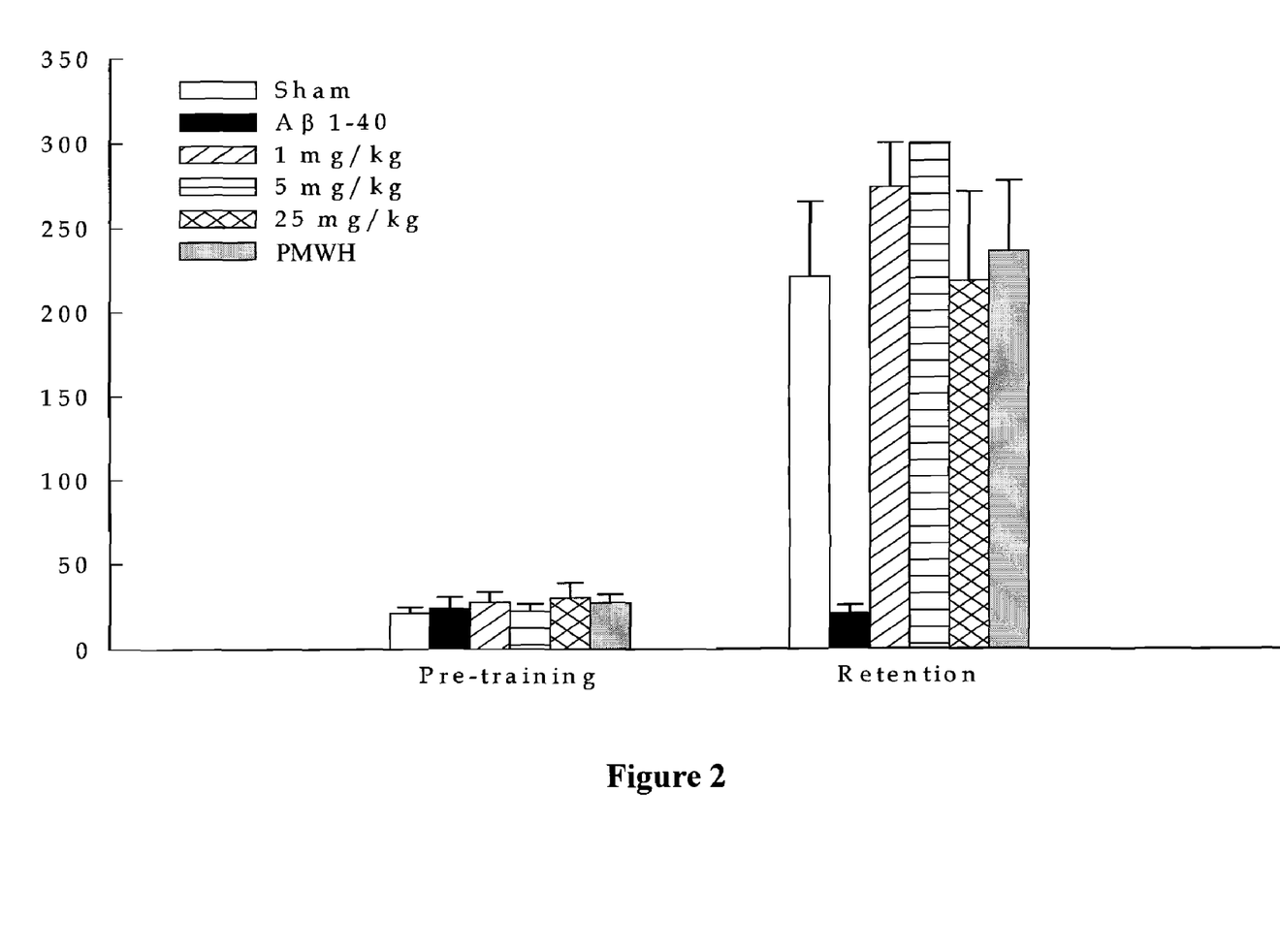
FIG. 2 shows the results of the passive avoidance test.
Figure 3:
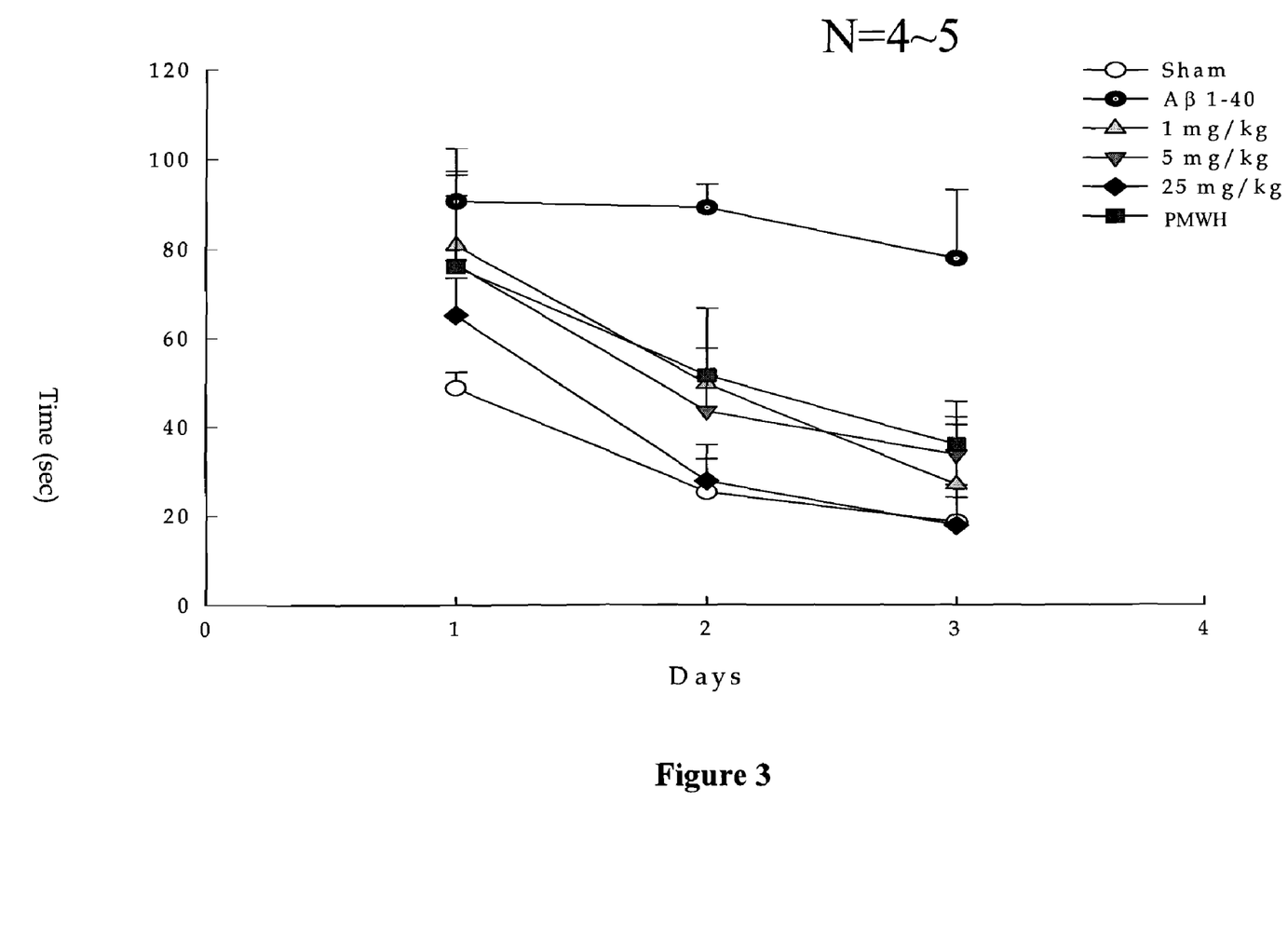
FIG. 3 shows the results of the spatial manipulating ability of the water maze test.
Figure 4:
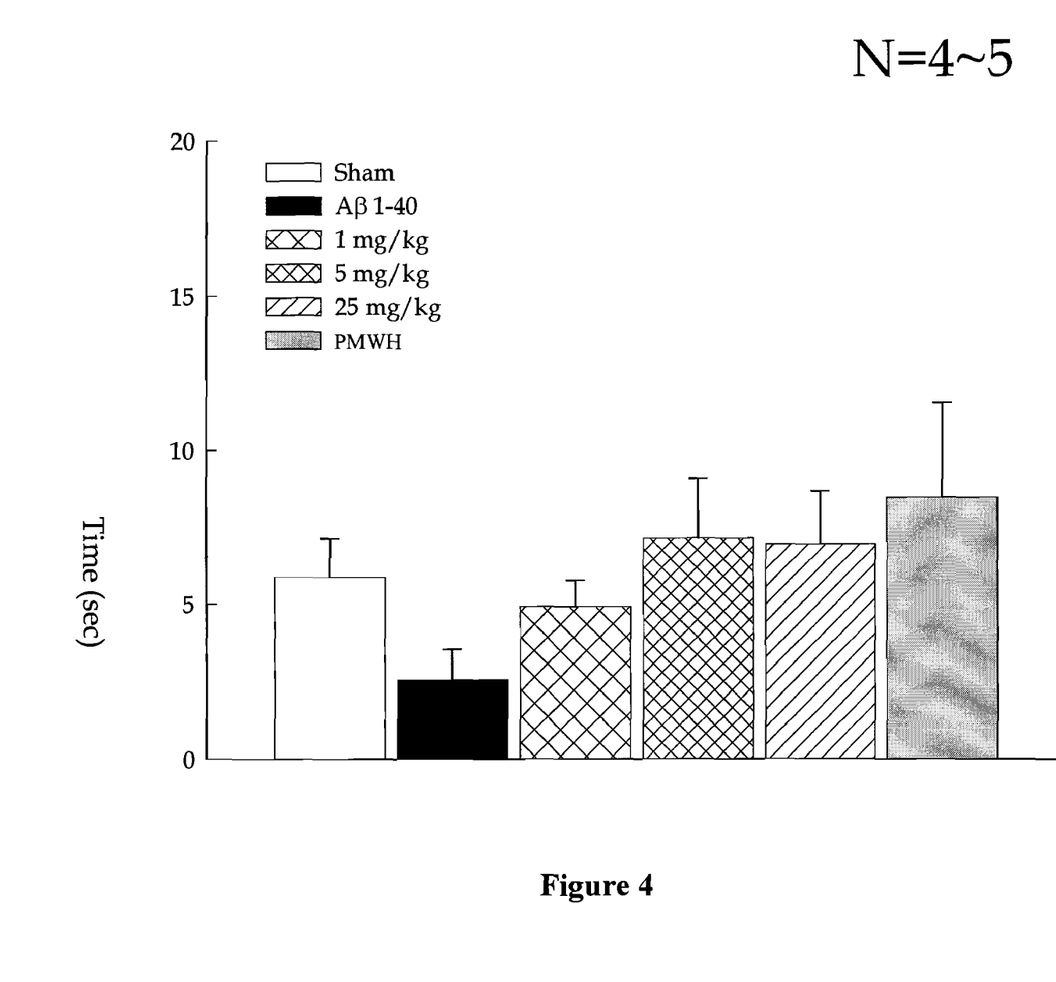
FIG. 4 shows the results of the working memory of the water maze test.

The results of the passive avoidance test were shown in FIG. 2. The results of the learning and memory ability were shown in FIG. 3 and the results of the reference memory of the water maze test were shown in FIG. 4. As observed in FIGS. 2 to 4, the rats in the control groups (Sham) did not show cognitive behavior impairments, whereas the Aβ 1-40-induced dementia rats treated with placebo (Group Aβ 1-40 shown in the figures) developed severe cognitive behavior impairments. It was found that PM903 (1, 5 and 25 mg/kg body weight) efficiently improved the passive avoidance and spatial memory of Aβ 1-40-induced dementia rats. The effective dosage of PM903 is from 1 to 25 mg/kg body weight. Compared to the positive control (Group PMWH shown in the figures), the effective dosage of PM903 is reduced more than 20 fold.

What is claimed is:

1. A process for preparing a *Polygonum multiflorum* extract comprising the steps of:
   a) extracting the *Polygonum multiflorum* herb with an ethanol solution of about 10 to 30 v/v % or methanol to obtain a *Polygonum multiflorum* crude extract;
   b) diluting the crude extract obtained by step a) with water to obtain a diluted crude extract having a final alcohol concentration of about 2 to 5 v/v %;
   c) loading the diluted crude extract of step b) into a resin column;
   d) eluting the *Polygonum multiflorum* extract from the column with one or more alcohol solutions of about 10 to 100 v/v %; and
   e) collecting and combining the eluted fractions to obtain a refined *Polygonum multiflorum* extract.

2. The process of claim 1, wherein the *Polygonum multiflorum* herb is a dried or processed *Polygonum multiflorum* herb.

3. The process of claim 1, wherein the alcohol solution is an ethanol, methanol or isopropanol solution.

4. The process of claim 1, wherein the resin is macroporous resin or gel resin.

5. The process of claim 4, wherein the macroporous resin is DIAION HP-20 resin.

6. The process of claim 4, wherein the gel resin is a Sephadex LH-20 resin.

7. The process of claim 1, wherein the extraction of step a) is conducted at room temperature.

8. The process of claim 1, wherein the extraction of step a) is conducted at a pH of about 5.3.

9. The process of claim 1, wherein the alcohol solution of step a) is an ethanol solution of about 10 to 30 v/v %.

10. The process of claim 1, wherein the alcohol solution of step a) is a methanol solution of about 20 to 95 v/v %.

11. The process of claim 1, wherein the alcohol solution of step d) has a concentration of about 30 to 70 v/v %.

12. The process of claim 1, wherein the alcohol solution of step d) has a concentration of about 35 to 50 v/v %.

13. The process of claim 1, wherein the alcohol solution of step d) is a methanol solution of about 50 v/v %.

14. The process of claim 1, wherein the alcohol solution of step d) is an ethanol solution of about 35 v/v %.

15. The process of claim 1, wherein the alcohol solution of step d) is a ethanol solution of about 50 v/v %.

16. The process of claim 1, wherein the *Polygonum multiflorum* extract obtained in step e) comprises about 65 to 85 w/w % of 2,3,5,4'-tetrahydroxystilbene-2-O-β-D-glucoside (TSG) and about 5 to 10 w/w % of catechin.

17. A *Polygonum multiflorum* extract prepared by the process according to claim 1.

18. The *Polygonum multiflorum* extract of claim 17, which comprises about 65 to 85 w/w % of TSG and about 5 to 10 w/w % of catechin.

19. The *Polygonum multiflorum* extract of claim 17, which comprises less than about 0.5 w/w % of emodin and less than about 0.2 w/w % of emodin-8-β-D-glucoside.

20. A composition comprising a therapeutically effective amount of the *Polygonum multiflorum* extract according to claim 17 and optionally a pharmaceutically acceptable carrier, diluent or excipient.

21. The composition of claim 20, which further comprises one or more other anti-dementia agents.

22. A method for treating dementia comprising administering a composition according to claim 20 to a subject in need thereof.

23. The method of claim 22, wherein the dementia is selected from the group consisting of aging-related dementia, Alzheimer's disease, vascular dementia, and minor mental and intellectual disorders.

24. The method of claim 22, wherein the *Polygonum multiflorum* extract is administrated at a dose of about 1 to 25 mg/kg body weight.

* * * * *